United States Patent [19]

Rebar

[11] Patent Number: 5,016,307
[45] Date of Patent: May 21, 1991

[54] INTEGRAL STRETCHER AND INTRAVENOUS FLUID CARRIER/GRAVITY DEPENDENT DRAINAGE SUPPORT

[76] Inventor: Linda Rebar, 3213 N. Kenmore, Apt. B, Chicago, Ill. 60611

[21] Appl. No.: 498,346

[22] Filed: Mar. 23, 1990

[51] Int. Cl.$^5$ .............................................. A61G 7/06
[52] U.S. Cl. ............................................. 5/503; 5/60; 5/86
[58] Field of Search ........................ 5/60, 86, 503, 508, 5/82 R; 248/297.5, 339; 296/20

[56] References Cited

U.S. PATENT DOCUMENTS

| | | | |
|---|---|---|---|
| 622,000 | 3/1889 | Greene | 5/508 X |
| 837,642 | 12/1906 | Powell | 5/503 X |
| 1,246,078 | 11/1917 | Ford | 5/503 X |
| 1,839,705 | 1/1932 | Schiffhouer et al. | 5/60 |
| 2,673,771 | 3/1954 | Krewen . | |
| 2,696,963 | 12/1954 | Shepherd . | |
| 2,935,286 | 5/1960 | Parsons . | |
| 2,957,187 | 10/1960 | Raia | 5/503 |
| 3,081,464 | 3/1963 | Lochner | 5/503 |
| 3,304,116 | 2/1967 | Stryker | 296/20 |
| 3,345,023 | 10/1967 | Scott et al. | 5/503 X |
| 3,709,372 | 1/1973 | Alexander . | |
| 3,709,556 | 1/1973 | Allard . | |
| 4,113,222 | 9/1978 | Frinzel . | |
| 4,179,159 | 12/1979 | Sicklucki et al. | 297/DIG. 4 X |
| 4,262,872 | 4/1981 | Kodet . | |
| 4,541,596 | 9/1985 | Price . | |
| 4,807,837 | 2/1989 | Gawlik et al. . | |

Primary Examiner—Michael F. Trettel
Attorney, Agent, or Firm—Leydig, Voit & Mayer

[57] ABSTRACT

A patient transportation apparatus is disclosed comprising a stretcher and a collapsible pole for use in supporting IV sets and the like. The pole portion of the apparatus is adjustable in height with respect to the plane of the stretcher while being capable of being collapsed to a position below or equiplanar with the horizontal surface of the stretcher. The pole is located so that in all positions it does not extend beyond the perimeter of the horizontal surface. In another embodiment a lower support means is also provided for supporting gravity dependent drainage bags and the like.

7 Claims, 2 Drawing Sheets

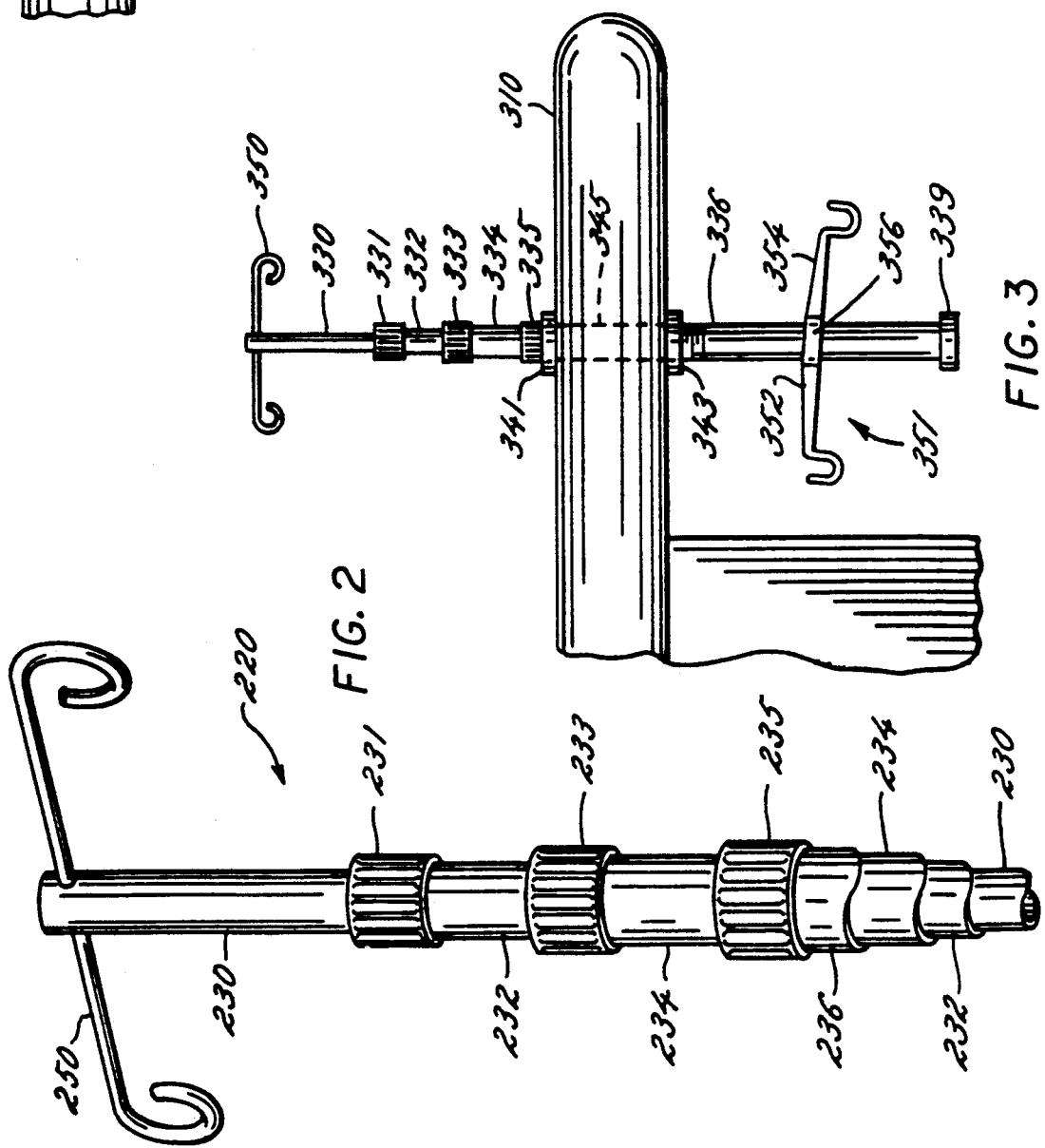

INTEGRAL STRETCHER AND INTRAVENOUS FLUID CARRIER/GRAVITY DEPENDENT DRAINAGE SUPPORT

FIELD OF THE INVENTION

This invention relates generally to medical devices such as stretchers and particularly to stretchers having integral poles for supporting medical apparatus such as intravenous infusion bags and the like.

BACKGROUND OF THE INVENTION

Since the inception of modern medical practice, the need to transport nonambulatory patients in a safe manner in emergency situations has existed. Presently, transportation of a nonambulatory patient is typically accomplished by use of a wheel chair, if the condition of the patient permits. If not, a gurney or stretcher equipped with wheels may be used to allow the patient to be transported through corridors or the like.

In certain emergency and critical care situations, a patient to be transported may also require a continuous intravenous infusion of blood or an infusion solution, such as 0.9% saline solution, 5% dextrose solution and the like. Typically, the solution for infusion is supplied in a bag or a bottle, which must be suspended above the patient to allow gravity-driven flow of the solution to the patient along intravenous infusion tubing. It is this periodic need to suspend a container of infusion solution above a patient located on a mobile carrier, such as a stretcher, that presents an amazingly complex problem.

Typically a container of intravenous infusion solution must be located from about 2 to about 3 feet above the level of the heart of the patient, to provide for adequate gravity flow of the solution to the patient. It should be readily apparent that having a fixed pole or the like, permanently attached to a mobile carrier, such as a stretcher simply is not a viable approach to the problem.

Although there is need to have a stationary means of holding an intravenous infusion set in place at certain times, at others times there is a dominating need to access the patient. It may be impossible to obtain adequate, critical access to a patient if a permanent device for holding the infusion set is employed. Also, it should be clear that if a fixed stanchion is used to support an intravenous infusion set, its mere physical presence may interfere significantly with a greater need for mobility of the patient.

Faced with the need to support IV infusion devices a substantial height above a patient, while maintaining both mobility as well as flexibility, many solutions have been suggested and some even tried. Exemplary of the previously proposed solutions are the following patents.

U.S. Pat. No. 2,696,963 relates to a portable intravenous fluid carrier designed to be attached to a stretcher or patient bed. The carrier comprises a collapsible pole which, if attached to a stretcher, protrudes outside the perimeter of the stretcher and does not collapse below the plane of the stretcher. Of similar design is U.S. Pat. No. 2,673,771 which relates to an infusion carrier for attachment to hospital stretchers. The infusion carrier comprises a pole which is attached to the stretcher outside the perimeter of the stretcher, presenting a safety hazard due to its unwieldy protrusion from the cart. Additionally, when the pole is collapsed, a substantial lower portion of the pole projects well above the plane of the stretcher, preventing free access to the patient. Such a configuration also is quite impractical for stretchers that must be collapsed for storage, such as the stretchers used in mobile emergency vehicles.

U.S. Pat. No. 2,935,286 relates to an infusion standard for attachment to a patient bed or the like. Although the standard is partially collapsible, it does not collapse below the plane of the bed to which it is attached. Additionally, the point of attachment of the device is outside the perimeter of the bed.

U.S. Pat. No. 2,957,187 relates to a telescoping stand with buttons located at the junctions of the respective pole segments, providing a rapidly releasable design. However, the pole is not used in combination with a stretcher or the like.

U.S. Pat. No. 3,709,372 relates to yet another intravenous supply container support. The ability to vertically adjust the height of the standard is provided by a mounting which permits the standard to be slid upwardly or downwardly and fixed in various positions. The pole, however, cannot be completely collapsed below the plane of the bed.

U.S. Pat. No. 3,709,556 relates to a telescoping IV pole which may be attached to wheel chairs and stretchers. When attached to a stretcher, the vertical standard may be lowered to a position below the plane of the stretcher, but must be fixed in a position outside of the perimeter of the stretcher in order to be raised to a position for supporting an intravenous infusion set. This configuration in operation provides a substantial physical obstacle to access to the patient and increases the effective dimension of the cart, thereby increasing the probability that the pole may accidentally strike a bystander, doorway or other obstruction.

U.S. Pat. No. 4,113,222 relates to a collapsible intravenous pole having a horizontal trigger bar which is centrally pivotally mounted and a clutch which retains the pole at a desired height unless the trigger bar strikes an object, causing the clutch to disengage, allowing the pole to telescope downwardly. The pole is not shown in conjunction with a stretcher and when illustrated in combination with a patient bed, the pole is not situated to collapse below the plane of the bed.

U.S. Pat. No. 4,262,872 relates to a collapsible pole assembly which includes a collapsible pole attached to a stretcher via a coupler to a pivotally mounted shank which allows the pole to be placed in a horizontal position for storage. This configuration does not allow the pole to collapse below the plane of the stretcher.

U.S. Pat. No. 4,541,596 relates to a portable intravenous pole for use in an emergency. The pole is foldable to a compact configuration but, if used in conjunction with a stretcher, it does not store below the plane of the stretcher. Further, the pole is not permanently attached to the stretcher.

U.S. Pat. No. 4,807,837 relates to a portable intravenous stand which is capable of telescoping in height. The stand is not designed for permanent attachment to a stretcher nor for collapsing below the plane of a stretcher to which the pole is attached.

Although some of the foregoing approaches have some degree of viability and potential, the true indication of their worth is their lack of acceptance in the medical profession. The stretcher design in most substantial use today, having the optional capability of supporting an IV infusion set, employs a removable support shaft. In some instances, the shaft is comprised of two hollow tubes, with the top tube being slidably adjustable within the lower tube portion.

A stretcher as described above allows one to remove the pole to provide for accessibility and ease of transportation. However, because the pole is totally removable, it can be easily set aside and misplaced. It is quite apparent that a stretcher which is missing the removable pole cannot support an IV set. Missing IV poles can quickly complicate an already difficult emergency situation and even jeopardize a patient's life. When emergency medical personnel must relegate time to seeking replacement IV poles, critical resources are wasted.

In an emergency situation, one cannot tolerate the possibility that a critically needed IV infusion may be delayed because of the lack of such a support means. From a practical viewpoint, the lack of a support structure for the IV set may mean that a needed critical care technician, such as a nurse, may be required to hold the IV bottle or the like above the patient, making it difficult or impossible for the nurse to also simultaneously render the needed critical care.

Further, misplaced or improperly stored IV poles also present significant potential for personal injury to unwary personnel. As one can imagine, an IV pole thoughtlessly placed on the floor or leaned precariously against a wall or the like, presents a significant safety hazard; yet, emergency medical personnel have as their primary responsibility attending to a patient and not proper storage of IV poles.

It is clear that loss, misplacement, and unavailability of IV poles currently presents substantial problems to the medical community. The expense alone of replacing lost and misplaced IV poles is staggering. Of more significance is the hidden cost of the time lost in trying to locate such missing IV poles.

With the present day approach to solving the problem of IV poles for use with stretchers, even if attendants have the time to follow the manufacturer's directions regarding proper storage of the IV pole, frustration still exists. Because the typical storage location is usually under the stretcher, medical personnel are required to squat, bend or kneel to even determine if the pole has been properly stored. Replacing the pole in the proper storage location also presents the problem in reverse, plus requiring the threading of the pole into the proper storage position, a feat of skill which if not cautiously performed, may endanger unfortunate bystanders in the area. Further, if the pole is not properly stored under the stretcher, injury to personnel may result when the pole falls from the stretcher.

Even if a medical attendant is lucky enough to find a properly stored pole waiting under the stretcher, the problems continue. The pole is taken in hand and the stretcher placed in position to be fitted with the pole. The end of the pole requires insertion into a defined support hole in the stretcher, but the support hole in the stretcher may be obscured by the patient, the mattress, other medical devices or parts thereof, siderails, tubing and the like, making the task frustrating, at best.

The correct placement of the pole into the support hole, under the best of conditions and luck, still requires the use of at least two, and sometimes three, hands. Unfortunately, as the medical technician focuses upon the task at hand, putting the pole into the support hole, enough attention may not be paid to the opposite end of the pole, which typically has a "T" configuration, capable of inflicting severe harm to bystanders and equipment alike.

Another set of problems result from the ability of the pole, in use, to freely rotate. Such free rotation results in the attached tubing winding around the pole, making removal of the IV bag or bottle difficult while placing stress on the connections which may result in inadvertent disruption of the flow of the IV solution to the patient. Also, because of the typical "T" configuration of the top of the pole, if the top is turned so that a support arm projects outwardly, perpendicular to the length of the stretcher, during movement of the patient, the support arm may become caught in doorways, or the like, or may strike passersby.

To date, few meaningful solutions have been suggested to the foregoing problems. At least one company has gone so far as to physically chain the IV pole or its top support portions to the stretcher. That may prevent loss, until someone breaks the chain, but it also introduces other safety problems. The top portion, when not in use, is free-hanging, and may freely swing in a dangerous manner. Also, its mere presence in unwanted locations presents the possibility of medical personnel becoming entangled with the chain of the support portion itself. The chain also causes restrictions in the movement and makes even more difficult and time consuming the task of inserting the pole into the support hole. Additionally, the chain itself poses infection control problems.

When a medical attendant is called upon to place the top portion of the IV pole in place for use, the task presents a potentially dangerous situation. One must be extremely cautious when inserting the pole into the support, not to hit the patient, other attendants, or critical care equipment. In an emergency situation, the problem becomes even more acute as pressure to administer medical care to a patient in need becomes more and more pressing and the magnitude of the problem only worsens.

Another approach to providing IV set support on an as-needed basis employs a pivotable IV pole which is of a one-piece construction. The pole in that design is hinged so that it may be placed in a horizontal position along-side the patient and mattress. That solution solves the problem of loss, but presents its own problems. For example, the patient or mattress may actually be on top of the pole when it is in the horizontal position. If the need then arises to use the pole, the patient, the mattress or both may need to be shifted away from the pole before it can be raised to the vertical position.

The foregoing sometimes presents more of a problem than one might imagine, especially if the patient is nonresponsive and must be physically moved by an attendant. Also, the counterpart problem exists when it becomes necessary to fold the tube down to the horizontal position for storage. If the patient, mattress or both are located over the side where the tube is to be stored, each must be moved before the pole can be stored out of the way.

From all of the foregoing discussion it is quite apparent that a significant need exists for a transportable IV pole and mobile stretcher device which overcomes the problems which have faced the medical profession for so long without solution.

SUMMARY OF THE INVENTION

There now has been discovered a patient transportation apparatus, comprising a stretcher and a collapsible stanchion pole for use in supporting IV sets and the like. The pole portion of the apparatus is adjustable in height with respect to the plane of the stretcher. The invention does not suffer from the problems associated with the prior art devices.

The stanchion is substantially perpendicular to and connected with said horizontal surface. The stanchion is capable of being extended above the plane of the horizontal surface and being collapsed to a position below or equiplanar with the horizontal surface. The stanchion is located so that in all positions, said stanchion does not extend beyond the perimeter of said horizontal surface.

The pole portion of the present invention is not readily removable from the stretcher, so it avoids the problem of being lost or misplaced. At the same time the pole can be completely collapsed so that it does not in any manner obstruct easy access to the patient. Of great importance, the pole is rapidly collapsible and rapidly extendable, as the need arises.

In another aspect of the present invention, there is provided for a stretcher, a means for supporting a gravity dependent drainage bag or the like, and associated apparatus. In such an instance a lower stanchion is connected to the lower side of the stretcher horizontal surface. The lower stanchion is located so that it does not extend beyond the perimeter of the horizontal surface. Typically, the lower stanchion is perpendicular to the stretcher horizontal surface, but it need not be in all instances. A lower support means is provided so that gravity dependent drainage bags and the like may be supported at a level below the plane of the horizontal surface. Preferably, the lower support means is slidably movable along the lower stanchion and is capable of being fixed in position at any point along the lower stanchion. In some instances the exterior of the lower stanchion may desirably be threaded as well as the interior of the annular ring forming a part of the lower support means. In such an instance the lower support may be adjusted in height by simple rotation of the lower support means.

BRIEF DESCRIPTION OF THE FIGURES

FIG. 2 is an exploded view of one embodiment of a stanchion of use in the present invention.

FIG. 3 is a side view of an embodiment of the present invention showing, the presence of a lower support means for supporting gravity dependent drainage bags and the like.

FIG. 4 is side view of an embodiment of the present invention showing the presence of a lower horizontal support means for supporting gravity dependent drainage bags and the like, without the presence of a vertical support for IV sets and the like.

DETAILED DESCRIPTION OF THE PREFERRED EMBODIMENTS

Figure 1:
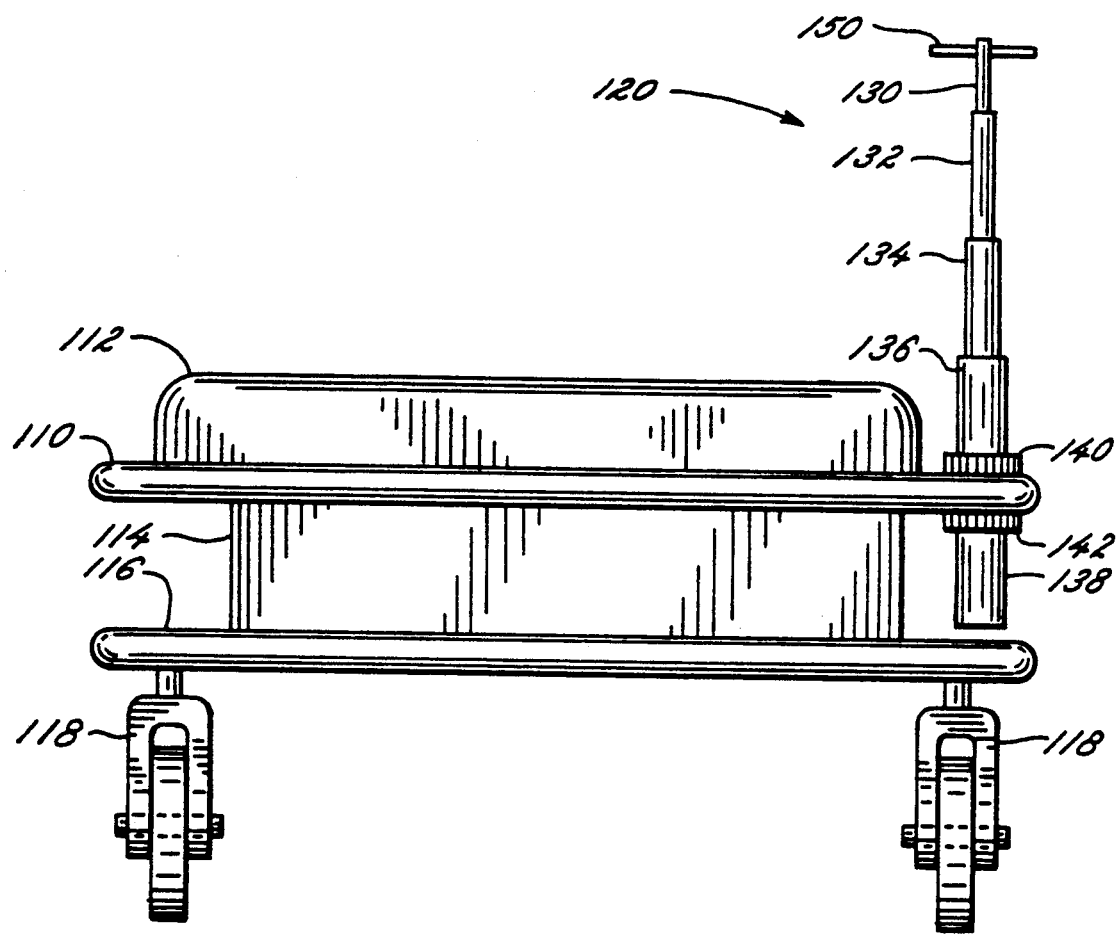
FIG. 1 is an end view of a stretcher and stanchion of the present invention.

In accordance with the present invention there is provided an apparatus comprising a stretcher and a self-storing, collapsible stanchion or pole combination. The stretcher may be of any standard configuration having a substantially horizontal surface for supporting a patient. The stanchion has a top portion which is collapsible and the entire stanchion is configured to be substantially perpendicular to the plane of the horizontal surface. The stanchion is positioned to pass through the horizontal surface at which point the stanchion is also connected to the stretcher. The top of the stanchion is capable of being extended above the plane of the horizontal surface and being collapsed to a position below or equiplanar with the horizontal surface. For purposes of the present invention, the term "plane of the horizontal surface" is meant to include not only the plane formed by the integral horizontal support which mechanically forms a part of the stretcher, but also the plane formed by any mattress or the like which is to be used to support the patient in some degree of comfort on top of the integral horizontal surface.

By virtue of the positioning of the stanchion as described in the foregoing, the stanchion, in all positions, fully extended, collapsed or intermediately extended, does not extend beyond the perimeter of said horizontal surface and does not create a physical protrusion which may inadvertently strike a passerby, attendant, doorway, or the like. Of course, if the top of the stanchion is fitted with a substantially horizontal supportment, forming a "T" configuration on the top of the stanchion, that support member itself may protrude outside of the perimeter of the horizontal surface.

The stanchion may be of any design which allows the top portion thereof to be extended above the plane of the stretcher for use and to be positioned or collapsed to a storage position below or equiplanar with the stretcher. Many stanchion designs exist in the art and may be readily adopted for use in the present invention. Thus, any of the stanchion designs as shown in U.S. Pat. No. 2,957,187 (spring-compressed button locking means), U.S. Pat. No. 3,709,556 (external thumb-screw locking means) or U.S. Pat. No. 4,807,837 (threaded, external compression fittings), the specifications of which are incorporated herein by reference, may be employed in the present invention.

Other automatically telescoping or manually operable designs may likewise be used, as the exact mechanism by which the stanchion may be raised or lowered is by no means critical. Thus, spring-loaded poles, in which the top portion of the stanchion only is spring-loaded is within the scope of the present invention, as well as designs in which the entire stanchion is spring-loaded, allowing for nearly immediate extension of the pole.

As only one of many possible embodiments of the present invention, FIG. 1 shows an end view of a stretcher and stanchion combination 100 of the present invention. In that figure, a horizontal surface 110 is provided for the stretcher which accommodates a mattress 112. The horizontal surface is supported by known adjustable-height support means 114 which allows the stretcher to move in a vertical direction. The support means 114 in turn is supported by a platform 116 to which wheel means 118 are attached to provide mobility to the cart.

Attached to the horizontal surface 110 is stanchion 120. The stanchion is comprised of an upper portion 130 which is slidably mounted within the remaining lower portion of the stanchion. Although the lower stanchion portion may be comprised of only one additional slidable element, as illustrated, the lower portion of the stanchion comprises slidable elements 132, 134 and 136, as well as a fixed lower support and housing member 138 which is fixed below the plane of the horizontal surface 130. As shown, the lower support and housing member 138 is attached to the horizontal surface 130 by means of external nuts 140 and 142 which are threaded onto external threads on member 138 to rigidly affix the stanchion to the surface. However, the stanchion may be affixed to the horizontal surface 130 by any convenient means.

The upper stanchion portion 130, as shown supports a generally horizontal IV support element 150 which may function to support IV bags, bottles and the like. The upper support element 150 may be capable of collapsing within upper stanchion portion 130 for storage or otherwise being storable or removable.

In FIG. 2, an exploded view of one embodiment of a stanchion 220 is illustrated. The stanchion comprises an upper portion 230 and a lower portion which is partially illustrated. As shown, the lower portion comprises slidable elements 232, 234 and 236 which are held in place by compression fittings having external nuts 231, 233 and 235. Additionally, the upper stanchion portion 230 is shown connected to upper IV support member 250 which may be removably mounted to the upper stanchion portion 230.

In FIG. 3, another embodiment of the present invention is illustrated in which the lower stanchion portion is also used to support a lower horizontal drainage support member 351. The upper stanchion portion 330 is connected to an upper IV support member 350. The upper stanchion support is comprised of slidable elements 332 and 334 which are slidably mounted within each other and within lower support and housing member 336. The lower stanchion, in the illustrated embodiment, comprises a lower slidable support means 351, slidably mounted on lower stanchion 336 which is threaded at 345 for a distance slightly longer than the depth of the horizontal support means 310. The lower stanchion 336 is attached to the horizontal support means 310 by means of retaining means 341 and 343 which are internally threaded and tightened to hold the lower stanchion 345 in place. The lower end of the lower stanchion is capped by a retaining means 339 which has an external diameter larger than the external diameter of the lower stanchion 336. Of course, the lower stanchion element 336 could be attached by any functional means. The lower support means 351 is comprised of two substantially horizontal support arms 352 and 354 which are joined at an annular ring 356 which has an interior diameter slightly greater than the exterior diameter of the lower stanchion 336.

In FIG. 4, there is illustrated a side view of an embodiment of the present invention in which only a lower gravity dependent drainage support system is coupled with a stretcher. In a fashion similar to that utilized with respect to the IV support means, lower stanchion 440 is attached to the bottom side of horizontal support means 410, via thread means 442 which may be inserted into mating threads located within the horizontal support means 410. Lower support means 450 is comprised of two horizontal support elements, 452 and 454, which are joined by an annular ring 456. The interior diameter of the annular ring is slightly greater than the exterior diameter of the lower stanchion 440 which allows the lower support means 452 to be slidably moved in a vertical fashion along the stanchion 440, when no weight is bearing upon either support element. When weight is applied to either support element, the annular ring 456 then binds on the exterior of the stanchion 440, causing fixation of the support element 450 at that point. A lower retention means or nut 444 having a diameter greater than the exterior diameter of the lower stanchion 440 is provided to prevent the support means 450 from being completely removed therefrom. Of course, the lower support means may be permanently fixed in height on the lower stanchion, rather than being slidably mounted. Also, the lower support need not be horizontal at all, so long as it in some manner provides support for gravity dependent drainage bags or the like.

In operation, the upper horizontal support element may be used to support IV solution containers, monitors, and other medical devices. When present, the lower horizontal support element may be used to support drainage bags or receptacle or other medical devices, as desired.

In all instances, the upper stanchion elements are slidably mounted so that they may be collapsed to a point that they are below or equiplanar with the horizontal support element. It is recognized that some small portion of the upper stanchion may protrude slightly, such as three inches, or less, above the plane of the horizontal surface. This may be necessary or desirable in order to accommodate, for example, the height of external compressive elements or the like used to fix the height of the stanchion. The term "equiplanar with the horizontal support surface" is meant to encompass such a slight protrusion above the actual plane of that surface.

By locating the stanchion within the perimeter of the horizontal support of the stretcher, in accordance with the present invention, the stanchion or pole does not protrude from the stretcher, presenting a safety hazard to hospital personnel and bystanders and avoids undesirable impact of the pole with doorways and the like.

Since the present invention allows the stanchion or pole to be stored below the plane of the horizontal stretcher surface, free access to the patient is provided. Moreover, because the pole is an integral part of the stretcher, lost and misplaced poles are completely eliminated. Of substantial importance, however, is the fact that the stretcher and stanchion combination of the present invention allows a single attendant to quickly raise or lower the pole, as needed. Also, because the pole is firmly attached to the stretcher and visible as well as accessible from a standing position, there is never uncertainty that the pole is ready and available in an emergency situation.

In the embodiment of the present invention in which a lower gravity dependent drainage support is present, a medical attendant may quickly and easily set up a gravity dependent drainage set, such as that used to drain fluids from a patient located on the stretcher. Because a lower stanchion is permanently fixed to a stretcher itself, it is also available. The lower support element, being slidably mounted, allows the attendant to rapidly adjust the height of the drainage bag to meet the individual specific needs of a particular situation. Because the lower support element is slidably mounted when no weight is bearing upon it, an attendant may, without great distraction, adjust the element to the appropriate height and immediately place on one of the support elements, the drainage bag or receptacle, quickly fixing the location of the lower support on the lower stanchion. This may be done with one hand without the need to divert an attendant's attention from other tasks which may be being performed concurrently.

What is claimed is:

1. A patient transportation apparatus comprising a stretcher having a substantially horizontal surface with a perimeter for supporting a patient and a vertically collapsible stanchion; said stanchion being substantially perpendicular to and connected with said horizontal surface inside said perimeter; a stanchion housing being connected with said horizontal surface directly below said stanchion, the stanchion being capable of being extended above the plane of the horizontal surface and being collapsed within said stanchion to a position below or equiplanar with the horizontal surface; the stanchion being located so that in all positions, including all intermediate, partially collapsed positions of said stanchion, said stanchion does not extend beyond the perimeter of said horizontal surface.

2. The apparatus of claim 1 further comprising a means for supporting a gravity dependent drainage bag which comprises a lower stanchion which is connected to the lower surface of the stretcher horizontal surface, positioned so that the lower stanchion does not extend beyond the perimeter of the horizontal surface and a lower support means connected to said lower stanchion.

3. The apparatus of claim 2 wherein the lower support means is adjustable in height.

4. The apparatus of claim 3 wherein the lower support means comprises an annular ring having an interior diameter slightly larger than the exterior diameter of the lower stanchion and at least one support arm connected thereto, the difference between the diameter of the interior of the annular ring and the exterior diameter of the lower stanchion being sufficiently small so that upon application of weight to said support means, the annular ring becomes fixed in position with respect to the lower stanchion.

5. A patient transportation apparatus comprising a stretcher having a substantially horizontal surface for supporting a patient and a means for supporting a gravity dependent drainage bag which comprises a lower stanchion which is connected to the lower surface of the stretcher horizontal surface, positioned so that the lower stanchion does not extend beyond the perimeter of the horizontal surface and a lower support means connected to said lower stanchion.

6. The apparatus of claim 5 wherein the lower support means is adjustable in height.

7. The apparatus of claim 6 wherein the lower support means comprises an annular ring having an interior diameter slightly larger than the exterior diameter of the lower stanchion and at least one support arm connected thereto, the difference between the diameter of the interior of the annular ring and the exterior diameter of the lower stanchion being sufficiently small so that upon application of weight to said support means, the annular ring becomes fixed in position with respect to the lower stanchion.

* * * * *